(12) United States Patent
McDaniel

(10) Patent No.: US 7,004,933 B2
(45) Date of Patent: *Feb. 28, 2006

(54) ULTRASOUND ENHANCEMENT OF PERCUTANEOUS DRUG ABSORPTION

(75) Inventor: David H. McDaniel, Virginia Beach, VA (US)

(73) Assignee: Light BioScience L.L.C., Virginia Beach, VA (US)

( * ) Notice: Subject to any disclaimer, the term of this patent is extended or adjusted under 35 U.S.C. 154(b) by 386 days.

This patent is subject to a terminal disclaimer.

(21) Appl. No.: 09/876,157

(22) Filed: Jun. 8, 2001

(65) Prior Publication Data

US 2002/0120225 A1 Aug. 29, 2002

Related U.S. Application Data

(60) Division of application No. 09/168,683, filed on Oct. 9, 1998, now Pat. No. 6,398,753, which is a continuation-in-part of application No. 09/087,146, filed on May 29, 1998, now Pat. No. 6,030,314.

(51) Int. Cl.
*A61M 31/00* (2006.01)

(52) U.S. Cl. .......................... 604/506; 604/22; 604/500

(58) Field of Classification Search ............. 604/46, 604/500, 506, 22, 20, 501, 890.1
See application file for complete search history.

(56) References Cited

U.S. PATENT DOCUMENTS

| | | | |
|---|---|---|---|
| 4,458,678 A | 7/1984 | Yannas et al. |
| 4,646,743 A | 3/1987 | Parris |
| 4,767,402 A | 8/1988 | Kost et al. |
| 4,888,354 A | 12/1989 | Chang et al. |
| 4,930,504 A | 6/1990 | Diamtopulos et al. |
| 4,969,912 A | 11/1990 | Kelman et al. |
| 5,021,452 A | 6/1991 | Labbe et al. |
| 5,037,432 A | 8/1991 | Molinari |
| 5,198,465 A | 3/1993 | Dioguardi |
| 5,226,907 A | 7/1993 | Tankovich |
| 5,231,975 A | 8/1993 | Bommannan et al. |
| 5,266,480 A | 11/1993 | Naughton et al. |
| 5,332,802 A | 7/1994 | Kelman et al. |
| 5,336,498 A | 8/1994 | Snider |
| 5,397,352 A | 3/1995 | Burres |
| 5,423,803 A | 6/1995 | Tankovich et al. |
| 5,425,728 A | 6/1995 | Tankovich |
| 5,445,146 A | 8/1995 | Bellinger |
| 5,445,634 A | 8/1995 | Keller |
| 5,460,939 A | 10/1995 | Hansbrough et al. |
| 5,591,444 A | 1/1997 | Boss, Jr. |
| 5,620,478 A | 4/1997 | Eckhouse |

(Continued)

FOREIGN PATENT DOCUMENTS

ZA  97/7751  *  8/1997

OTHER PUBLICATIONS

*Laser in Surgery and Medicine*, 21:262–268 (1997), Improvement of Host Response to Sepsis by Photobiomodulation, Wei Yu et al (marked up).*

(Continued)

*Primary Examiner*—Manuel Mendez
(74) *Attorney, Agent, or Firm*—Morrison & Foerster LLP

(57) ABSTRACT

A system for enhancing and improving the transcutaneous or transdermal delivery of topical chemicals or drugs. A disposable container contains a substantially sterile unit dose of an active agent adapted for a single use in a medical treatment. The unit dose is formulated to enhance transport of the active agent through mammalian skin when the active agent is applied to the skin and the skin is exposed to light and/or ultrasound defined by at least one specific parameter.

1 Claim, 7 Drawing Sheets

U.S. PATENT DOCUMENTS

| | | | |
|---|---|---|---|
| 5,643,334 A | * | 7/1997 | Eckhouse |
| 5,658,323 A | * | 8/1997 | Miller |
| 5,660,836 A | | 8/1997 | Knowlton |
| 5,660,850 A | | 8/1997 | Boss, Jr. |
| 5,665,372 A | | 9/1997 | Boss, Jr. |
| 5,669,916 A | * | 9/1997 | Andersen |
| 5,683,380 A | * | 11/1997 | Eckhouse et al. |
| 5,686,112 A | * | 11/1997 | Liedtke |
| 5,752,949 A | * | 5/1998 | Tankovich et al. |
| 5,755,752 A | | 5/1998 | Segal |
| 5,817,089 A | * | 10/1998 | Tankovich et al. |
| 5,843,072 A | * | 12/1998 | Furumoto et al. |
| 6,030,374 A | * | 2/2000 | McDaniel ................... 604/506 |

OTHER PUBLICATIONS

*J. Dermatol. Surg. Oncol.*, 13:2, Feb., 1987, Biostimulation of Wound Healing by Lasers: Experimental Approaches in Animal Models and Fibroblast Cultures, R. Patrick Abergel et al. (marked up).*

*Lasers in Surgery and Medicine*, 12:528–537 (1992), Power Density and Exposure Time of He–Ne Laser Irradiation are More Important than Total Energy Dose in Photo–Biomodulation of Human Fibroblasts in Vitro, Hans H.F.I. van Breugel et al.*

Skin barrier Principles of Percutaneous, Absorption, Hans Schaefer et al. 1996., pp. 153 and 175 (marked up).*

*Skin Pharmacol*, 1994; 7:130–139, High Frequency Sonophoresis: Permeation Pathways and Structural Basis for Enhanced Permeability, Gopinathan K. Menon et al. (marked up).*

*Anesthesiology*, V. 78 No. 6, Jun. 1993, Use of Ultrasound to Enhance the Local Anesthetic Effect of Topically Applied Aqeous Lidocaine, Katsuro Tachibans et al. (marked up).*

*Journal of the American Podiatric Medical Association*, vol. 82, No. 8, Aug. 1992, Hydrocortisone Phonophoresis, A Literature Review, Joseph T. Newman et al. (marked up).*

*Science*, vol. 269, Aug. 1995, Ultrasound–Mediated Transdermal Protein Delivery, Samir Mitragotri et al. (marked up).

*Pharmaceutical Research*, vol. 8, No. 2, 1991, Influence of Ultrasound on the Percutaneous Absorption of Nicotinate Esters, Heather A. Benson et al. (marked up).

*Physiotherapy*, vol. 74, No. 11, Nov., 1988, Transmission of Ultrasound Energy Through Topical Pharmaceutical Products, Heather A.E. Benson et al. (marked up).

*Journal of Pharmaceutical Sciences*, vol. 84, No. 6, Jun., 1995, A Mechanistic Study of Ultrasonically–Enhanced Transdermal Drug Delivery, Samir Mitragotri et al. (marked up).

*Pharmaceutical Research*, vol. 9, No. 8, 1992, Somophoresis, II. Examination of the Mechanisms of Ultrasound–Enhanced Transdermal Drug Delivery, D. Bommannan et al. (marked up).

The International Congress of Esthetics, Oct. 25–27, 1997, convention program.

*Cosmetics & Toiletries*, vol. 113, Jun.,. 1998, Ultrasonic Radiation for Hair Treatments, Miklos M. Bruer.

*J. Appl. Cosmetol.*, vol. 15, 147–159, Oct.–Dec. 1997, Enhancing the Glycolic Acid Efficacy by Piezoelectric Vibrations, P. Mortganti et al. (marked up).

*Rheumatology and Rehabilitation*, 1975, 14, 237, The Stimulation of Protein Synthesis in Human Fibroblasts by Therapeutic Ultrasound, W. Harvey et al. (marked up).

*Physical Therapy*, vol. 75, No. 7, Jul. 1995, In Vitro Effects of Therapeutic Ultrasound on the Nucleus of Human Fibroblasts, Patrick G. De Deyne et al.

*The Lancet*, Jul. 25, 1987, A Controlled Trial Weekly Ultrasound Therapy in Chronic Leg Ulceration, M.J. Callam et al., pp. 204–206 (marked up).

*Am. J. Phys. Med. Rehabil.*, vol. 68 No. 6, Dec. 1989, The Effects of Therapeutic Ultrasound on Tedon Healing, Chukuka S. Enwemeka.

*Acta Chirurgiae Plasticae*, 19, 3–4, 1977, Ultrasonic Effect on Collagen Synthesis and Deposition in Differently Localized Experimental Gramulomas, J.E. Purkyne (marked up).

*Infections in Surgery*, Sep., 1982, Stimulation of Tissue Repair by Therapeutic Ultrasound, Mary Dyson.

*Arch Phys Med Rehabil.*, vol. 73, Jul. 1992, Low Dose Ultrasound Effects of Wound Healing: A Controlled Study with Yucatan Pigs, Nancy N. Byl, et al. (marked up).

*Physiotherapy*, Apr. 1978, vol. 64, No. 4, Stimulation of Tissue Repair by Ultrasound: A Survey of Mechanisms Involved, Mary Dyson et al. (marked up).

*Acta Chirurgiae Plasticae*, 15, 2, 1973, Strengthning of Sutured Skin Wound with Ultrasound in Experiments on Animals, V. Drastichova et al.

*Ultrasonics*, Jan., 1980, The Role of Ultrasound–Induced Cavitation in the In–Vitro Stimulation of Collagen Synthesis in Human Fibroblasts D.F. Webster et al. (marked up).

*Ultrasound in Med. & Biol*, vol. 4 pp–343–351, The Role of Cavitation in the In Vitro Stimulation of Protein Synthesis in Human Fibroblasts by Ultrasound, D.F. Webster et al. (marked up).

*J. Dermatol Sci.*, Mar. 1996, 11(3):250–253, Ascorbic Acid Preferentially Enhances Type I and III Collagen Gene Transcription in Human Skin Fibroblasts, Takima S. Pinnel (Abstract).

*J. Photocem Photobiol B*. Feb. 1993; 17(2):109–114, Photodynamic Effects on the Nuclear Envelope of Human Skin Fibroblasts, B. Krammer et al. (Abstract).

*J. Biochem (Tokyo)*, Nov., 1984; 96(5)1491–1500, Hemoprotein H–450 Indentified as a Form of Cytochrome P–450 Having an Endogenous Ligand at the 6th Coordination Position of the Heme, T. Omura (Abstract).

*Laryngoscope*, Dec., 1987, 7(12):1454–1459, Biostimulative Effects of Nd:YAG Q–Switch Dye on Normal Human Fibroblasts Cultures: Study of a New Chemosensitizing Agent for the Nd:YAG Laser, D.J. Castro et al. (Abstract).

*Vojnosanit Pregl.*, Nov., 1995; 52(6):539–546, Stimulatory Effect of Low–Power Density He–Ne Radiation of Human Fibroblasts in Vitro, M. Hrnjak et al. (Abstract).

*Ann Plast Surg.* Jan., 1987; 18(1):47–50, Biostimulation of Wound Healing in Vivo by a Helium–Neon Laser, F.R. Lyons et al. (Abstract).

*Lasers Surg Med.* 1997; 20(1):56–63, Effects of Photostimulation on Wound Healing in Diabetic Mice, W. Yu et al. (Abstract).

*Artif Cells Blood Substit Immobil Biotechnol.* Jul., 1998; 26(4):437–439, In Vitro Experimental Research of Rabbit Condrocytes Biostimulation with Diode Laser Ga–Al–As: a Preliminary STudy, G. Morrone et al. (Abstract).

*Lasers in Surgery and Medicine*, 22:281–287 (1998), Laser Photostimulation of Collagen Production in Healing Rabbit Achilles Tendons, G. Kesava Reddy et al. (Abstract).

Lasers in Surgery and Medicine, 22:294–301 (1998), Stimulatory Effect of 660 nm Low Level Laser Energy on Hypertrophic Scar–Derived Fibroblasts: Possible Mechanisms for Increase in Cell Counts, Cecilia Webb et al. (Abstract).

Lasers Surg Med. 1992; 12(5):528–537, Power Density and Exposure Time He–Ne Laser Irradiation are More Important than Total Energy Dowse in Photo–Biomodulation of Human Fibroblasts in Vitro, H.H. Van Bruegel et al. (Abstract).

Voinosanit Pregl. No., 1995; 52(6):539–546, Stimulatory Effect of Low–Power Density Ne–Ne Laser Radiation on Human Fibrblasts in Vitro, M. Hrnjak et al. (Abstract).

Dermatol Surg., 1998; 24:1383–1386, The Use of Low Energy Photon Therapy (LEPT) in Venous Leg Ulcers: Double–Blind Placebo–Controlled Study, Aditya K. Gupta et al.

Lasers Surg. Med., 1997; 20(2):131–141, Thermal Damage Assessment of Blood Vessels in a Hamster Skin Flap Model by Fluorescent Measurement of a Liposome–dye System, S. Mordon et al.

Laser Surg. Med., 1997; 21(4): 365–73, Selective Laser Photocoagulation of Blood Vessels in a Hampster Skin Flap Model Using a Specific ICG Formulation, S. Mordon et al.

Journal of Drug Targeting, 1994, vol. 2, pp. 405–410, Liposomes: A Novel Topical Delivery System for Pharmaceutical and Cosmetic Applications, N. Weiner et al.

Pharmacuetical Research, 1992, vol. 9. pp. 629–635, Adsorption of Fluorescein Dyes on Albumin Microspheres, Kamel Egbaria et al.

Pharmacuetical Research, vol. 10, No. 12, 1993, Site–Specific Drug Delivery to Pilosebaceous Structures Using Polymeric Microspheres, Alain Rolland et al.

Journal of Pharmaceutical Sciences, vol. 79, No. 6, 1990, Relationship Between Contact Time of Applied Dose and Percutaneous Absorption of Minoxidil from a Topical Solution, James Ferry et al.

Journal of Pharmaceutical Sciences, vol. 81, No. 8, 1992, Drug and Vehicle Deposition from Topical Applications:: Use of Vitro Mass Balance Technique with Minoxidil Solutions, Jui–Chen Tsai et al.

Journal of Pharmaceutical Sciences, vol. 78, No. 5, 1989, Transdermal Iontophoretic Drug Delivery; Mechanistic Analysis and Application to Polypeptide Delivery, V. Srinivasan et al.

Science, vol. 270, 1995, Chemical Generation Of Acoustic Waves: A Giant Photoacoustic Effect, Huxiong Chen et al.

The Journal of Investigative Dermatology, vol. 103, No. 2, 1994, Effects of Ascorbic Acid on Profileration and Collagen Synthesis in Relation to the Donor Age of Human Dermal Fibroblasts, Charlotte Philips et al.

Journal of Pharmaceutical Sciences, vol. 58, No. 9, 1969, Enhancement of Percutaneous Absorption by the Use of Volatile: Nonvolatile Systems as Vehicles, M.F. Coldman et al.

Xenbiotics, vol. 17, No. 9, 1113–1120, Deposition of Viprostol (a Synthetic PBE2 Vasodilator) in the skin Following Topical Administration to Laboratory Aminals, G. Nicolau et al.

Meth and Find Exp Clin Pharmacol, 1989; 11(1): 643–646, Percutaneous Absorption of Coumarin, Griscofulvin and Propranolol Across Human Scalp and Abdominal Skin, Wolfgang Ritschel et al.

The Journal of Investigative Dermatology, vol. 99, No. 1, 1992, Topical Delivery Enhancement with Multilamellar Liposomes into Pilosebaceous Units: I. In Vitro Evaluation Using Florescent Techniques with the Hamster Ear Model, Linda Lieb et al.

Arch Dermatol, vol. 121, Feb. 1985, Percutaneous Absorption of Minoxidilin Man, Thomas Franz.

Skin Pharmacol, 1991; 4:230–234, Percutaneous Penetration of Methyl Nicotinate at Three Anatomic Sites: Evidence for an Appendageal Contribution to Transport, Ethel tur et al.

Journal of Pharmaceutical Sciences, vol., 79, No. 7, 1990, Iontophoresis of Polypeptides: Effect of Ethanol Pretreatment of Human Skin, V. Srinivasan et al.

Skin Pharmacol, 1994; 7:245–256, Percutaneous Absorption of Estradiol and Progesterone in Normal and Appendage–Free Skin of the Hairless Rat: Lack of Importance of Nutritional Blood Flow, F. Hueber et al.

Journal of Pharmaceutical Sciences, vol. 82, No. 2, 1993, Iontophoretic Transdermal Delivery of Salicylic Acid and Licodaine to Local Subcutaneous Structures, Pariminder Singh et al.

Arch Dermatol Res, 267, 229–235 (1980), Variations in Percutaneous Absorption of Testosterone in Rhesus Monkey Due to Anatomic Site of Application and Frequency of Application, Ronald Wester et al.

Pharmaceutical Research, vol. 9, No. 7, 1992, Transdermal Delivery of Insulin to Allosxan–Diabetic Rabbits by Ultrasound Exposure, Katsuro Tachibana.

Photodermatol Photoimmunol Photomed, 1991:8:129–134, Effects of Ultaviolet A and B on the Skin Barrier: a Functional, Electron Microscopic and Lipid Biochemical Study P. Lehman et al.

Arch Dermatol, vol. 127, Jan. 1991, Ultrasound Localization of Calcium in Psoriatic and Normal Human Epidermis, Gopinathan K. Menon et al.

British Journal of Dermatology, 1982, 107, 35–42, A Fluorescence Photographic Photomeric Technique to assess Stratum Corneum Turnover Rate and Barrier Function in vivo, A Finlay et al.

Physiological Review, vol. 51, No. 4, 1971, Permeability of the Skin, Robert Scheuplein et al.

Mag.–Bull, 1987, pp. 130–131, Noise–Induced Hearing Loss in Humans as a Function of Serum Mg Concentration, Z. Joachims et al.

Clin. Cardiol, 20, 285–290 (1997), Electrophysiology, Pacing and Arrhythmia, Dan Roden, MD.

The Yale Journal of Biology and Medicine, 58 (1985), 553–559, Regulation of Collagen Biosynthesis by Ascorbic Acid: A Review, Sheldon Pinnell.

Archives of Biochemistry and Biophysics, vol. 295, No. 2, 1992, pp. 397–403, Ascorbic Acid and Transforming Growth Factor–B1 Increase Collagen Biosynthesis via Different Mechanisms: Coordinate Regulation of Proal(1) and Proa1(III) Collagens, Charlotte Phillips et al.

Archives of Biochemistry and Biophysics, vol. 307, No. 2, 1993, pp. 331–335, Ascorbic Acid and Collagen Synthesis: Rethinking a Role for Lipid Peroxidation, Douglas Darr et al.

Toxicology and Applied Pharmacology, 94, 93–103, 1988, In Vitro percutaneous Absorption in Mouse Skin: Influence of Skin appendages, J. Kao et al.

*Journal of Pharmaceutical Sciences*, vol. 80, No. 5, 1991, Follicies Plan an Important Role in Percutaneous Absorption, Brigette Illel et al.

*Journal of Pharmaceutical Sciences*, vol. 81, No. 7, 1992, Studies of In Vitro Skin Permeation and Retention of a Leukotriene Antagonist from Topical vehicles with a Hairless Guinea Pig Model, Saran Kumar et al.

*Ultrasound in Med. Biol.*, vol. 22, No. 2, pp. 151–164, 1996, Physical Characteristics and Biological Effects on Laser–Induced Stress Waves, A. Doukas et al.

*J. Soc. Cosmet. Shem.*, 29, 265–282, May 1978, Autoradiographic Study on Percutaneous Absorption of Several Oils Useful for Cosmetics, M. Suzuki et al.

*Lasers in Surgery and Medicine*, 20:426–432, 1997, Effects of Low–Energy Gallium–Aluminum–Arsenide Laser Irradiation on Cultured Fibroblasts and Keratincytes, M. Pogrel et al.

*Advance Rehabilitation*, Jul/Aug. 1991, More Than a Thermal Modality: Ultrasound, Stephen Guffey et al.

*Electrotheraphy*, vol. 11, No. 4, Jul./Aug. 1991, Ultrasound: Current Concepts, Nancy Gann.

*The Journal for Prevention adn Healing Advances*, vol. 9, No. 5, Sep./Oct. 1996, Promotion of Wound Healing with Electrical Stimulation, Luther Kloth et al.

*Advance for Physical Therapists*, Mar. 23, 1992, Iniformity Needed in Therapeutic Use of Ultrasound, Michelle Pronsati.

*JOSPT*, vol. 12, No. 3, Mar. 1995, Temperature Changes in Deep Muscles of Human During Ice and Ultrasound Therapies: an In Vivo Study, David Draper et al.

Reprint from the *Journal*, Physikalische Medizin und Rehabilitation Heft Sep. 1968, The Combined Application of Ultrasound and Stimulation Currents, K. Gierlich et al.

*Advance Rehabilitation*, Apr., 1995, From Submarines to Rehab: New Developments in Ultrasound, John Murphy.

Department of Anatomy, Guy's Hospital Medical School, London, England, pp. 110–122; The Effect of Ultrasound on the Rate of Wound Healing and the Quality of Scar Tissue, M. Dyson.

The Twentieth Annual Pharmaceutics Graduate Student Research Meeting, The University of Missour–Kansas School of Pharmacy, Jun. 10–12, 1988, The Effect of Ultrasound on the In Vitro Penetration of Ibuprofen Through Human Epidermis, Maulik Nanavaty et al.

*In Vitro Cell, Dev. Biol.*, 28A:679–681, Nov.–Dec., 1992, Productive–Delivering Liposomes Specifically Target Hair Follicles in Histocultured Intact Skin, Lingna et al.

* cited by examiner

"Normal"

Lipid Bilayers (normal spacing)

"With Cavitation Bubbles"

Lipid Bilayers (increased space) or permeability

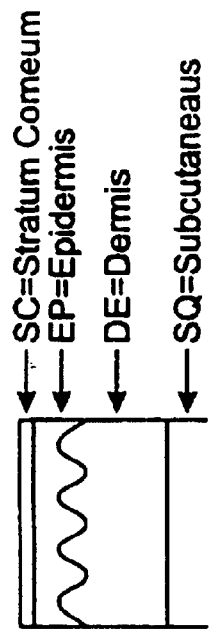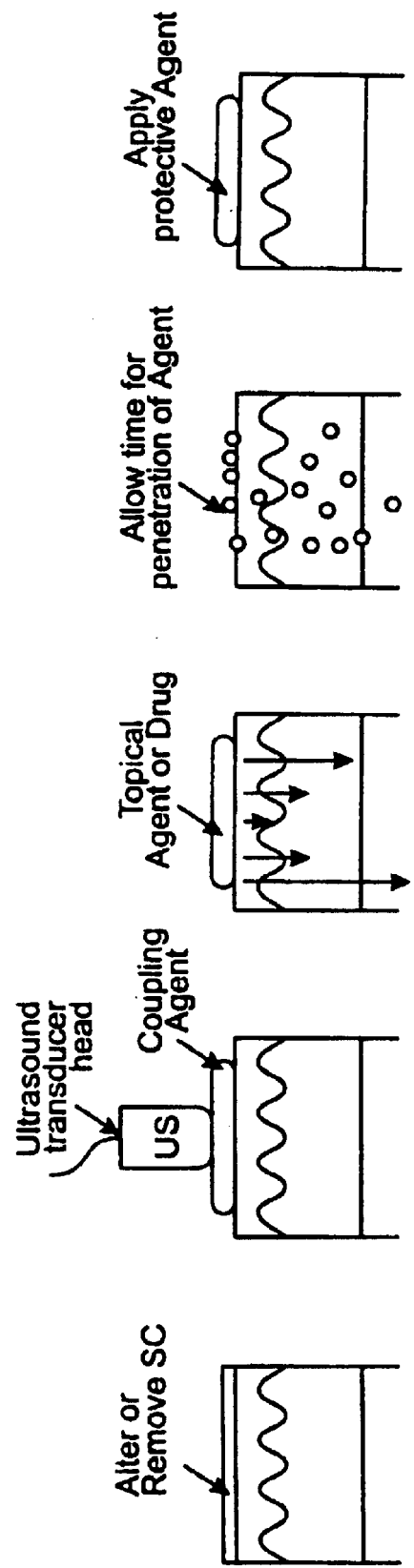
Figure 5

| Pigment Lightening Treatment - Facial Skin - Sensitive | | | | | |
|---|---|---|---|---|---|
| | Initial TX | Week 2 | Week 4 | Week 6 | Week 8 |
| Step 1<br>Enzyme 5min | Enzyme 5min | Enzyme 10min | Enzyme 10min | Enzyme 10min | Enzyme 10min |
| Step 2<br>Ultrasound<br>0.35W<br>5 min | | 0.35W<br>7 min | 0.35W<br>10 min | 0.50W<br>10 min | 0.50W<br>10 min |
| Step 3<br>Skin Lightening Agent<br>1.0/5min | | 1.0/10 min | 2.0/10 min | 2.0/10 min | 2.0/10 min |
| Step 4 | | | | | |

Figure 10

ULTRASOUND ENHANCEMENT OF PERCUTANEOUS DRUG ABSORPTION

FIELD OF THE INVENTION

The present invention generally relates to a system for enhancing and improving the transcutaneous or transdermal delivery of various topical chemicals or drugs (also referred to herein as "active agents").

BACKGROUND OF THE INVENTION

Heretofore, ultrasound has been primarily used for diagnostic purposes with an outstanding safety record. It has also been used for dental care. Physical therapy uses ultrasound primarily to generate deep heat and also sometimes as an adjunct to wound healing. Some attempts have been made since the 1950's to use ultrasound to deliver hydrocortisone into joint spaces (originally for bursitis) or lidocaine (for pain relief rather than injecting with needles. The current use of ultrasound to deliver drugs is primarily its use in physical therapy for non-invasive treatment of certain musculoskeletal disorders. Research in recent years has dramatically increased the understanding of ultrasound and its effects on skin and transport of topical agents. However, there is no consensus on how to optimally increase the flux or flow of topical agents across the skin using ultrasound.

Although ultrasound has been useful to deliver drugs very deeply into joints, several problems exist with this technique. For example, if high frequency ultrasound is directed toward a bone for an extended period of time, then the energy can cause a burn. To some extent a focused beam tends to cause uneven concentration and uneven penetration, and may also cause injuries. This is particularly true with older ultrasound equipment, but is also true of many current ultrasound technology in clinical use today. An additional problem with some earlier ultrasound equipment is that a two to four hour exposure period may be required. The newer ultrasounds use frequencies that provide results in a five to twenty minute time frame.

The use of ultrasound to deliver agents transcutaneously is generally termed "sonophoresis" but occasionally is termed "phonophoresis". Ultrasound generally comprises high-frequency sound waves that are above the human hearing range (usually greater than 20,000 Hertz (Hz) frequency units).

The sound waves may be generated by applying an alternating high frequency electrical current to a crystal such as a quartz, silicone dioxide, lithium sulfate of barium titanate. This current distorts the crystal, creating high frequency vibrations known as the piezoelectric effect. The sound waves produced have energy and may penetrate matter, depending on its acoustic density and composition. These sound waves may be delivered either in a focused manner and concentrated to a focal point (similar to the effects achieved with a magnifying lens and sunlight) or delivered in a non focused manner, termed "collimated," whereby the beam is uniform and parallel with no focal point (similar to falling rain).

The depth of penetration of ultrasound is inversely related to the frequency. Current diagnostic and therapeutic ultrasound typically ranges in frequency from 1–3 MHZ to 4–10 MHZ. Delivery may be pulsed in bursts or continuous beam modes, either stationary or continuously moving (usually at a rate of about one inch per second). The energies used generally range from a few milliwatts to a few watts.

The ultrasound energy is usually delivered through a transducer head. When used on skin, it is usually placed in direct contact with the skin using a coupling medium (which is often an aqueous gel), as shown, for example, in FIG. 1.

It is also known that topical agents may be applied directly to the skin. Sometimes absorption of these agents may be enhanced by techniques such as occlusion with synthetic materials (e.g. plastic), or transport may be enhanced by using low level electrical means such as galvanic current application or the technique of ionophoresis.

One problem with this known methodology is that of achieving more effective beneficial therapeutic clinical effects with topical agents by reaching higher concentrations in the dermis without damaging the dermis and/or the epidermis. Such damage may include undesirable and intolerable side effects such as flaking, peeling, persistent redness or burning.

The problem has not been adequately solved by simply using topical agents in various vehicles at higher strength. Using solutions at higher strength may tend to magnify the side effects. Using solutions at higher strength may also worsen internal systemic side effects. Simply using solutions at higher strength tends to work too broadly, and generally fails to selectively cause the desired effect.

Ionophoresis tends to work only if the molecules can be broken up into positive and negative ions and then driven in. A primary disadvantage of this technique is that many drugs cannot be broken up into positive and negative ions. Another disadvantage is that many drugs lose their effectiveness if broken up in this manner.

It has been proposed that drugs may be injected into the skin using a hypodermic needle. However, a primary disadvantage of this technique is that it generally fails to deliver the drug uniformly.

It has been proposed that drugs may be taken orally. However, in many cases this technique is not practical. For example, oral ingestion of vitamin C generally fails to provide a sufficiently high concentration of the drug in the skin. The technique may also involve certain risks. For example, oral ingestion of vitamin A derivatives may cause liver damage or birth defects.

It can be seen, therefore, that while the drugs themselves may be quite effective if used selectively, each of the traditional routes has one or more inherent limiting factors which prevent or inhibit the drugs from achieving their maximum effectiveness.

SUMMARY OF THE INVENTION

In accordance with the present invention, these and other objectives may be achieved by providing an optimal selection of ultrasound parameters such as frequency, intensity, pulse length, beam characteristics and application time on the skin (including both human and animal) to enhance the transport of topical agents into epidermal, dermal and subcutaneous tissues. The present invention may be useful to produce higher concentrations of such an agent than may be accomplished by current topical application or delivery methods. Such increased concentrations may have beneficial effects depending on the characteristics of the topical agent delivered. Patients who cannot tolerate current topical application methods may achieve beneficial effects by delivering similar concentrations of the agent with little or no side effects. Topical agents which cannot normally penetrate the skin with current methods may be transported into the dermis The effects of ultrasound on skin result from the release of energy. These include the non-thermal effects of (1) cavitation, (2) mechanical stress as well as (3) thermal effects.

It appears that ultrasound exposure in the therapeutic range causes cavitation in the keratinocytes of the stratum corneum as the primary effect in increasing skin permeability for transcutaneous transport of topical agents (cavitation is a process where bubbles are formed which oscillate causing structural disorder of the intercellular lipid bilayers of the keratinocytes).

In effect, this process is somewhat analogous to loosening the "mortar between the bricks" and expanding the "spaces between these bricks" so that the topical agent has a transport pathway to reach the epidermis and the deeper dermis of the skin. Drug molecules that are too large to penetrate the skin at all when applied topically may achieve significant penetration when used in conjunction with sonophoresis with proper parameters. See FIG. 3 and 4.

BRIEF DESCRIPTION OF THE DRAWINGS

A detailed description of a preferred embodiment of the present invention will be made with reference to the accompanying drawings.

FIG 5 illustratres the structure of the epidermal layers of human skin.

FIG. 5A illustrates an example of a pretreatment of the stratum corneum.

FIG. 5B illustrates an example of a coupling agent being applied and an ultrasound treatment being performed.

FIG. 5C illustrates an example of a coupling agent being removed and an active topical agent being applied.

FIG. 5D illustrates an example of an active topical agent being removed after an appropriate time.

FIG. 5E illustrates an example of a protective topical agent being applied.

FIG. 10 is a tabular illustration of a treatment regiment according to an illustrative embodiment of the invention.

DETAILED DESCRIPTION OF THE PREFERRED EMBODIMENTS

Figure 1:
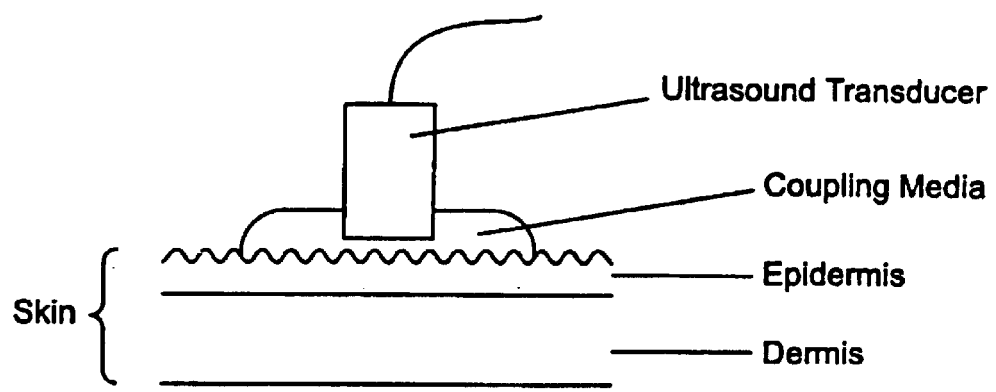
FIG. 1 illustrates an example of the delivery of ultrasound energy through a coupling medium and a transducer head.
Figure 2:
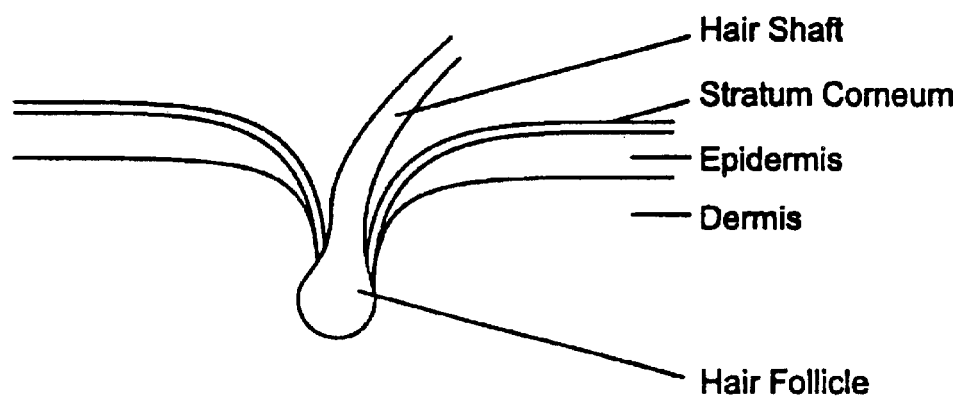
FIG. 2 illustrates an example of the percutaneous delivery of topical agents being principally limited by the barrier function of the stratum corneum (the outermost 15–25 microns of the skin).
Figure 3:
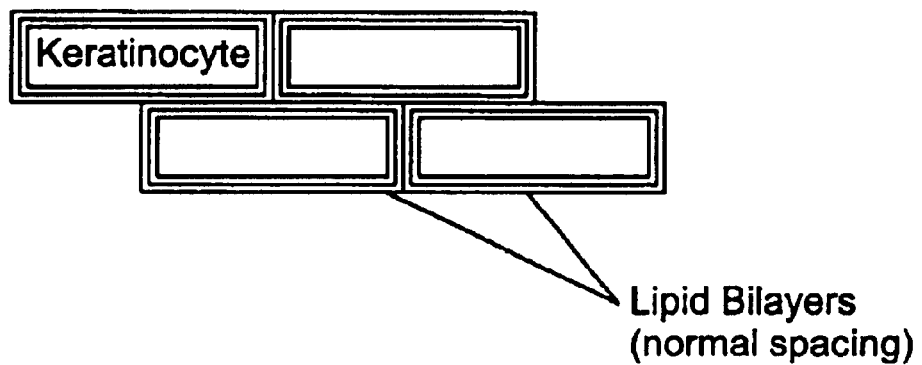
FIGS. 3 and 4 illustrate an example of cavitation from ultrasound "expanding" the spaces between keratinocytes, thus creating a channel for drugs including drug molecules that are too large to penetrate the skin when applied topically achieving significant penetration when used in conjunction with sonophoresis with proper parameters.

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, each active agent may be specially formulated to achieve a desired result using ultrasound. At present, many drugs are formulated to achieve a desired result using topical penetration, but the inventor is unaware of any drug that is specially formulated to achieve a desired or optimal result using ultrasound. At present, a coupling agent must typically be useful to enable effective transmission using ultrasound.

In a preferred embodiment each active agent may be provided in a single dose container or packet. The packet may preferably contain only a pure active agent, at an optimal strength and/or at an optimal concentration for a specific use. The active agent may be dissolved in an appropriate vehicle medium, such as a gel or a liquid. All other contaminants (including, for example, preservatives, fragrances, etc.) are preferably absent or removed from the packet. The need to include, with the active agent, additives for prolonging shelf life, improving stability, preventing spoilage, improving texture, etc., is thereby eliminated. In a preferred embodiment of the invention everything is removed from the active agent formulation which does not have a desired effect. Each packet is preferably packaged in a sterile manner, by radiation sterilization or other means. Additionally, the parameters of the collimated ultrasound are preferably selected for maximum safety. Preferably, exposure times are confined to intervals of five, ten, fifteen or twenty minutes.

In this preferred embodiment a layer of the active agent may first be placed on the skin. The ultrasound equipment may be adjusted to the optimize the ultrasound parameters, including the exposure time, and then turned on. The ultrasound wand may be moved gently over the skin for the duration of the selected exposure time. The treatment is essentially complete at the end of the selected exposure time. Any active agent residue left on the skin may be cleansed with a gentle cleansing agent, so that no active agent is left to irritate the skin. Treatment may be repeated at periodic intervals.

In another embodiment of the invention an ultrasound gel or similar substance may be put on the skin first. The skin may then be exposed to ultrasound. The gel may be removed and the active agent may be placed on the skin. The active agent may be allowed to sit on the skin for a period of time, preferably between about five and twenty minutes. This tends to provide a short "burst" of the active agent at a higher penetration. The residue may then be wiped off, so that no active agent is left to irritate the skin.

Another option would be to apply the active agent in a 'delivery device' such as a biomembrane, dressing or band-aid, liposome-polymer complex, aerosol spray dressing which functions as a delivery device, but also provides a barrier function. In this option, the active agent would be left on the skin for a period of hours or perhaps overnight.

It appears that, at least in this embodiment, the increased barrier spreading on the cells and/or permeability may last for up to one or two days. A topical agent, aerosol agent, dressing, or delivery device may be applied to help protect during this time or to help restore the barrier function. A preferred formulation could be a lipid mixture such as cholesterol, ceramides, free fatty acids, linoleic acid. Another option would be a lipid or liposome—polymer mixture or aerosol polymer coating. Consequently, the skin may be relatively absorbent and it may be preferable to provide some associated aftercare, such as avoiding sunburn, Retin-a or aftershave. Treatment with a topical agent specifically formulated to "restore" or improve barrier function may be used. Such a topical agent may also be packaged as described above.

In another embodiment of the invention an outer layer of skin may be removed before the skin is exposed to an active agent or ultrasound. This tends to enable the active agent to penetrate better and/or deeper. This may be achieved, for example, by first wiping the skin with acetone to strip the oils out. An enzyme may then be useful to selectively remove and/or kill only dead skin cells. Pretreatment with heat, skin hydrating preparations and preparations to alter (and optimize for treatment) the skin pH may also be utilized. Chemicals, abraders and lasers may also be used for this purpose, although they tend to be less discriminate. An active agent may then be placed on the skin and exposed to ultrasound, or the skin may be exposed to ultrasound prior to placing an active agent on the skin. The active agent may then be wiped off. The barrier function of the outer skin layer tends to return within a few hours or days.

It has been found that removing impediments to the introduction of an active agent to the skin tends to have at least one of the following three effects: (1) increasing the amount of active agent which enters the skin, (2) shortening the time during which the skin must be exposed, and/or (3) increasing the penetration depth of the active agent. Precision, uniformity and safety may be improved by reducing variations in the material actually placed on the skin and having the ultrasound beam as uniformly distributed as possible.

Treatment in accordance with the present invention tends to be relatively safe, relatively inexpensive, does not necessarily need to be performed by a physician, has a recovery time which is relatively short (and in many cases non-existent), and can be done repeatedly with virtually no cumulative adverse effects but with cumulative beneficial effects.

The present invention may provide a safe, effective delivery mechanism for a wide variety of active agents, including bleaching cremes, vitamin C, the vitamin A family, and topical anesthetics. In some cases the present invention may allow topical anesthetics to be administered in sufficient strength that scalpel work may be performed without needles. The present invention may be used for the treatment of leg ulcers, where the known effects of ultrasound alone may be useful to stimulate wound healing and treatment in accordance with the present invention may be useful to drive one or more new agents which enhance, speed or stimulate wound healing in to greater depths, producing results that are better and/or faster.

The packets may be provided in different sizes. For example, the size of one packet may be configured so that there is sufficient active agent in the packet to treat the average face. As another example, packet size may be configured so that there is sufficient active agent in the packet to treat the arms and/or legs. The packet may be configured for unit dose delivery, and the active agent may be optimized both for its vehicle and its percentage.

If two or three active agents are used in combination, or if some of the active agents are dissolved in micro spheres or synthetic devices, then the penetration ratio may be affected by the coefficients of diffusion and characteristics that are unique for each active agent, including molecular size and shape. If two or more active agents are used in combination, then each active agent may not necessarily be driven into the skin at the same ratio because each molecule may be driven in at a different rate. When several active agents are used in combination, some active agents may be driven in to higher strengths than others based on factors including their weight, their volume, their size, their shape and other properties. These factors may be optimized to achieve the desired treatment effect.

The active agent may be useful to stimulate biological systems, and from a disease therapeutic standpoint the active agent may also be useful to inhibit or turn off certain biological functions. In other words, the present invention may be useful to provide an active agent concentration of sufficient magnitude that it may cause a feedback inhibition. For example, if a concentration of 2% in the skin provides stimulation and a concentration of 4% is considered optimal, then it is possible that a concentration of 10% may provide less effect than 4% and at 15% the reverse effect may occur. It is therefore possible to have an active agent formulation (and/or time period and/or set of parameters) optimized so that the treatment does not merely restore biological function but actually treats disease.

Figure 4:
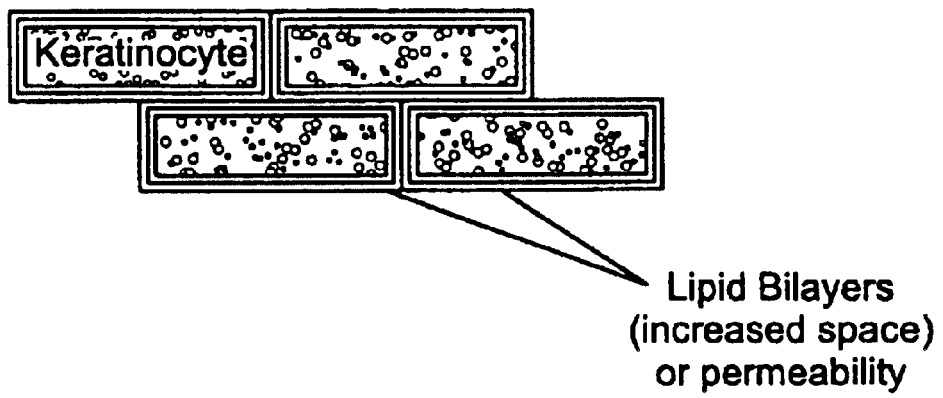
Figure 6:
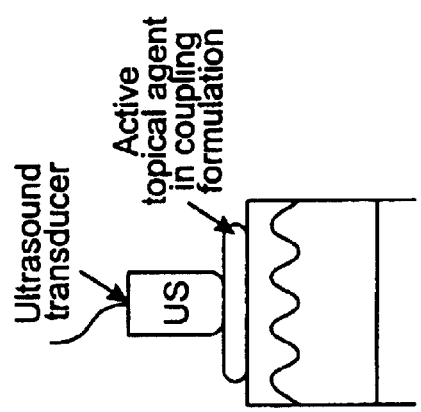
FIG. 6 illustrates an example of an active topical agent which also serves as a coupling agent being applied, and an ultrasound treatment being performed.
Figure 7:
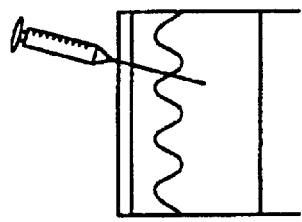
FIG. 7 illustrates an example of an injection of a drug or agent or autologous or donor fibroblast rich preparation.
Figure 8:
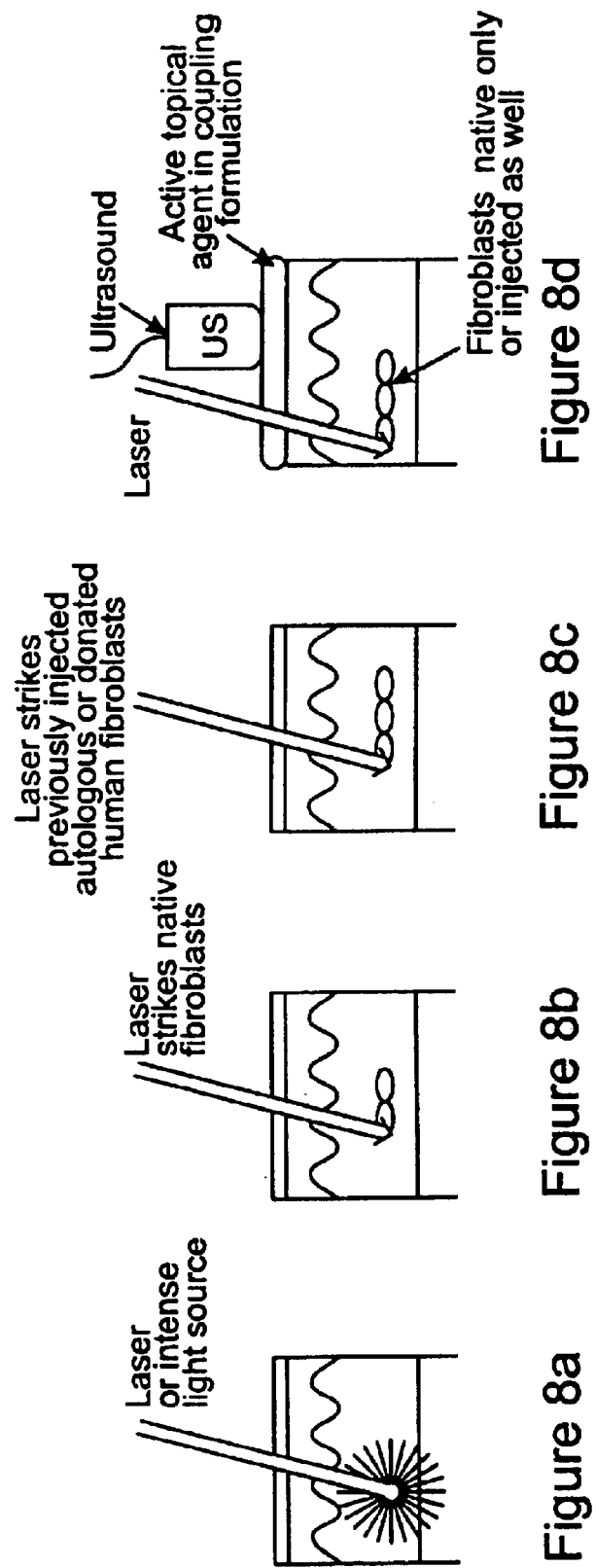
FIGS. 8A, 8B, 8C and 8D illustrate examples of an embodiment using low energy laser therapy to stimulate (directly or indirectly) the production, proliferation, activation, or inhibition of the activity, structure or function of various biochemical or photochemical or biological processes (this example features stimulation of a human fibroblast).
Figure 9:
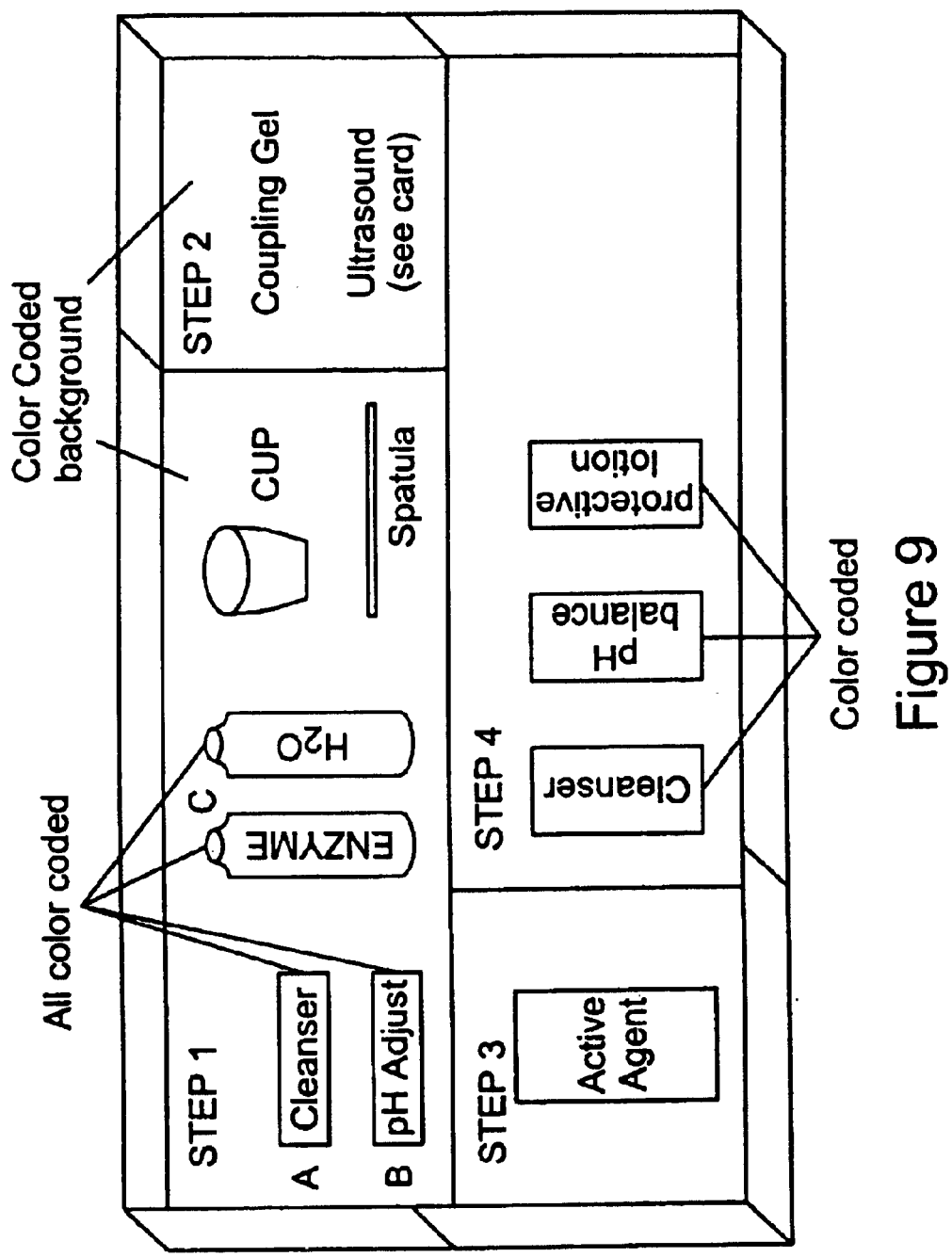
FIG. 9 shows an example of a system that may be used in accordance with an embodiment of the present invention.

The embodiment illustrated in FIG. 4 is primarily as a 'biostimulating' process and not a destructive or ablative process, such as commonly used in today's art. Using laser therapy or ultrasound (or both) to produce heat at a subnecrotic damage or injury threshold is other possible embodiment. (An example might be trying to achieve a dermal temperature that affects collagen—perhaps beginning around 55–60° C.

FIG. 4 illustrates an example of an embodiment using low energy laser therapy to stimulate (directly or indirectly) the production, proliferation, activation, or inhibition of the activity, structure or function of various biochemical or photochemical or biological processes so as to result (directly or indirectly) in effects that are beneficial to the structure, function or appearance of the skin and/or subcutaneous tissues or which results in the "rejuvenation" of photoaged, environmentally damaged or disease or drug/therapy altered skin or subcutaneous tissue.

The present invention, in a preferred embodiment, may be used either as a pretreatment followed by topical application of a desired agent or used in a coupling media vehicle to directly deliver the desired agent. At present, topical pharmaceutical products are not generally formulated in such a way as to optimize their efficiency as ultrasound couplants.

A preferred formulation for an "active" coupling agent is one which would best meet the criteria described for the optimal active agent alone, and yet would still provide an effective coupling function for an ultrasound transducer head.

The present invention, in a preferred embodiment, formulates these topical agents in concentrations and vehicles so as to be optimally effective when used in conjunction with sonophoresis. These specifications may vary with molecular size as well as diffusion and partition coefficients and other factors and may be uniquely formulated for each agent. The preferred embodiment for many may be a gel. Also preferred is individual single use sterile dose packets, thereby avoiding the need for preservatives and other additives that may cause undesirable effects or side effects.

The goal in many cases may be to maximize percutaneous transmission of the active agent. The following principles may be useful in selecting these formulations, except in some situations where a milder or submaximal effect or transmission may be desired for a given agent or situation.

In such case, the formulation may be shifted or modified to have reduced effect. Also, certain complex or synthetic delivery systems may follow different principles, such as lipid bilayers (liposomes) or synthetic polymers (microsponges).

However, for many situations the preferred formulation may be based upon the desire to approach, but not quite reach, a saturated solution of the active agent(s). Thus, the rate of release of active agent or drug may be greater in vehicles in which it exhibits poorest solubility. This may be more important than the total concentration, so as to maximize bioavailability and release.

In a preferred formulation, it may be desirable to select a vehicle which poorly solubizes the active agent and which preferably may evaporate at such a rate that the concentration of the active agent increases to offset the release into and through the stratum corneum. However, it may also be important that it not evaporate so quickly as to precipitate out on the skin, since this may decrease or even stop transport (situations where stable, supersaturated solutions form may be acceptable). Thus, it may be desirable to have sufficient non-volatile vehicle to avoid precipitation from occurring during the time the active agent may be applied to the skin. Since the transport rate may be affected by various factors, such as those described herein, the optimal vehicle may vary not only with each specific active agent, but also with the specific technique parameters (or disease state) since the barrier function (and thus transport depletion of concentration of active agent in vehicle) may vary.

Preferred ultrasound parameters may be determined in accordance with both efficacy and safety requirements. For example, one preferred range for lower frequency ultrasound may be between about 25 kHz and about 3 MHZ at about 0.5–2.0 W/cm$^2$ (either continuous or pulsed, using about a 20–25% duty cycle if pulsed). A preferred setting within this range may be at about 1.0 MHZ at about 2.0 W/cm$^2$, with a continuous wave beam and a treatment time of between about five and ten minutes. A preferred setting within this range for non-continuous beam (i.e. pulsed delivery) may be at about 1.0 MHZ at about 0.2–0.5 W/cm$^2$ with a 20–25% duty cycle with around a 2.0–20.0 msec "on" cycle and a treatment time of about five and ten minutes. One preferred range for higher frequency ultrasound may be between about 3 MHZ and about 16 MHZ at about 0.2–1.0 W/cm$^2$ (either continuous or pulsed, using about a 20% duty cycle if pulses), with a treatment time of between about one and twenty minutes. A preferred setting within this range may be at about 10 MHZ at about 0.2 W/cm$^2$, with a continuous treatment time of between about five and twenty minutes.

In a preferred embodiment the beam profile may be a collimated beam with precise control of output. In an alternative embodiment a focused beam may also be suitable. A preferred embodiment may provide a feedback warning if the operator loses contact with the skin, thus ensuring optimal treatment technique.

Further adjuncts to the process which increase permeability of skin or decrease skin barrier function may be helpful with optimizing the present invention. Options for this include, but are not limited to, stripping, removing, thinning or diminishing the structure, function, thickness or permeability of the stratum corneum by various mechanical, abrasive, photo acoustical, ablative, thermal, chemical, abrasive or enzymatic methods. Examples of these could include solvent or tape stripping, scrubbing, laser ablation or vaporization, chemical peeling, micro dermabrasion, enzyme peeling, or laser treatment using high peak power, short pulse duration lasers. A preferred embodiment may be enzyme peel, which is formulated to specifically remove only the dead stratum corneum cells.

In another embodiment of the invention sonophoresis may be used alone, without a topical agent, to produce a thermal effect (rather than to drive drugs in) to stimulate the skin (e.g. make fibroblasts, produce new collagen, elastin, etc.).

Examples of the active agent might include any of the following, either alone or in combination: Vitamin C; Vitamin E; Vitamin A; Vitamin K; Vitamin F; any of the various chemical forms and analogs; of these vitamins; Retin A (Tretinoin); Adapalene; Retinol; Hydroquinone; Kojic acid; various growth factors; echinacea; antibiotics; antifungals; antivirals; bleaching agents; alpha hydroxy acids; beta hydroxy acids; salicylic acid; antioxidant triad compound (with or without Tretinoin or Vitamin A derivatives); seaweed and salt water derived products antioxidants, phytuanthocyanims, phytonutrients, botanical and herbaceous products, hormones (including insulin), enzymes, minerals, growth factors, genetically engineered substances, cofactors or catalysts for various biological pathways and other antiaging substances, antibiotics, antifungals, and antivirals.

The active agents used in accordance with the present invention may be characterized by one or more of a variety of properties. Optimization of the active agents for use in accordance with the present invention may be achieved by the modifying one or more of these properties. The following are examples of some of the properties which may be modified, alone or in combination, to optimize active agents for use in accordance with the present invention:

Solubility—A sufficient concentration of active agent should preferably be dissolved in the selected delivery system vehicle or coupling agent for the desired treatment.

Stability—Some active agents may be unstable and may rapidly degrade after being dissolved in a vehicle or coupling agent. Therefore, in one preferred embodiment the active agent may be in the form of a powder (such as a freeze dried powder or lyophilized powder, for example) that is not mixed until treatment is imminent. Other instabilities may be related to oxidation from atmospheric oxygen or exposure to ultraviolet light or sunlight. Thus, in one preferred embodiment the active agent may be packaged under vacuum or nitrogen or another inert gas and may be packaged in a manner that protects the active agent from light.

Molecular Size—The active agent should preferably have a molecular size which enables it to penetrate the skin at the time of maximum permeability, and then should preferably be in a form which is either "active" or may become "activated" in the skin. For example, in the case of Vitamin C treatments, L-ascorbic acid has stability problems but is the active form in the skin and is a small molecule which enables penetration. In contrast, magnesium ascorbyl phosphate is very stable but is a much larger molecule and does not penetrate easily with current delivery systems. Guy & Potts have shown that the permeability of human (and mouse) stratum corneum may be determined by the molecular volume (weight) and the partition coefficient log poor.

pH—The activity of an active agent may frequently depend on an appropriate pH level. It is also important for skin to be at an optimal pH level. There is good evidence that the stratum corneum is much more permeable to neutral molecules than the salts of the weak acids or bases. Furthermore, skin enzymes and other processes may operate optimally at certain pH levels and poorly at others. For example, an enzyme preparation useful to remove stratum corneum may operate effectively at a pH level of 8.5. The skin may preferably be "pretreated" with a topical agent that increases the pH of the skin to this level. At the end of the treatment it may be advantageous to add another topical buffering solution or agent to "readjust" the skin back down to a normal skin pH level of 5.5.

pKa—The pKa tends to affect the amount of free acid and base in equilibrium, and thus has an impact on both the beneficial and adverse clinical effects of the active agent. A recent study by the FDA has shown that there may be considerable variation in the beneficial clinical effects (as well as the adverse and undesirable clinical side effects) of glycolic acid, even when the glycolic acid concentrations are the identical percentage. For example, if the pH of the glycolic acid preparation is adjusted to around 4.4 (approximately equal to the pKa of glycolic acid), then the ratio of beneficial to adverse side effects is much better than when the pH is lower than the pKa (and more free acid is available in the equilibrium). The pKa may vary for different compounds and thus may effect the choice of formulation.

Purity, Sterility, Absence of Nonactive Ingredients—The presence of an impurity (including chemical contaminants, preservatives, additives, fragrances, or micro-organisms, for example) may also potentially have enhanced penetration and thus produce undesired adverse or toxic effects.

Lipid Bi-Layer and Ionization—These may determine the "distribution" of the active agent, either in the lipid phase or in the ionized chemical form. These may affect diffusion and delivery of the active agent.

Lipophillic and Lipophobic—The choice of the delivery vehicle or coupling agent for the active drug may be effected by these properties of the active agent.

Diffusion Coefficient—One of the dominant factors in determining the transfer of the active agent into the skin, the Diffusion Coefficient measures the use of movement across the stratum corneum and the difference in concentration or percentage of active agent and also the thickness of the stratum corneum.

Partition Coefficient—One of the dominant factors in determining the percentage transfer of the active agent into the skin, the Partition Coefficient refers to the tendency for the active agent to leave its vehicle and enter the stratum corneum. The amount of material that moves across the units representative of stratum corneum and a given unit of time tends to be directly proportional to the Partition Coefficient as well as the Diffusion Coefficient.

In a preferred embodiment the invention may be provided in the form of a "treatment kit" prepackaged to contain all the appropriate topical agents, drugs, supplies, etc. needed for a specific treatment. The kit may be divided into compartments or zones. Each compartment may be coded by color, number or letter (for example), so that the compartments follow a "Step System" that guides the treatment provider (i.e., the nurse, esthetician, physician, etc.) through the treatment process. Within each color coded zone, individual products that are color coded to match that step color would be provided so that they would not be easily confused.

Each kit may be produced specifically for a certain active agent. Each kit may be produced specifically for a certain usage, based on disorder being treated, anatomic area, etc.

Treatment Regimen Cards may be included in the kit. The Treatment Cards may become a part of the patient record or chart. The Treatment Cards may enable the treatment provider to chart multiple, serial treatments. Such Treatment Cards may be useful to record basic information such as date of treatment, anatomic location, disorder, patient name, comments, etc. The Treatment Cards may also provide information regarding suggested treatment intervals, numbers of treatments, incremental increases in treatment parameters, incremental increases in active agent application time or strength.

Several different Treatment Cards may be included in a kit for a treatment provider to select. For example, a single kit may include different Treatment Cards for sensitive skin, regular skin, and post surgical skin treatment. These different Treatment Cards may have, as their distinguishing characteristics, differences in one or more of at least the following: percentage dilution of active agents, amount of time various agents or treatment are applied, or ultrasound or light source parameters, etc. Different Treatment Cards may be provided for different anatomic areas, such as the face, the arms or the legs, where these parameters may also be varied. Different Treatment Cards may be provided for different treatment options, for example gentle treatment for mild sun damage vs. aggressive treatment for severe sun damage.

The Treatment Cards may be color coded to indicate the time period for equipment parameters directly on the card. The Treatment Cards may also cross reference for percent concentration to the kit itself (in essence within each step of the kit) which may be color coded (for example pale blue background).

For example, there may be three levels of dilution or strength (mild, intermediate, maximal) which may be identified by a color code on the Treatment Card.

For example, at one step of the treatment the active agent may be mixed from a dry powder. The mixing instructions may be imprinted on the box for the dilution, and the Treatment Card may also indicate the recommended dilution. For example, a patient with sensitive skin receiving a series of six treatments may start at the most mild of the three dilution strengths for the first three treatments and then go to the intermediate for the last three. In contrast, a person with average skin might have the first two treatments performed at the mild strength, the third and fourth treatments at the intermediate strength, and the fifth and sixth treatments at the maximum strength. In that case weeks one and two of the Treatment Card may be one color to match the mild bar and the one background color, weeks three and four may be a different color to match the intermediate bar, and weeks five and six may be a third background color to match the maximum bar.

Another option may be to have colors, letters or numbers (for example 1.0, 2.0, 3.0, etc.) for the strengths of the kits where a dilution was not involved (for example cream or lotion that does not require mixing from a powder). In such a case, the patient Treatment Card background colors may correspond to the strength or color of the kit, rather than an individual dilution or compound of the kit. In such a case the cream may be in separate packages outside the kit, but still color coded. Likewise, different color bars may be useful to indicate the duration of the treatment in minutes, or the treatment parameters to be used on the ultrasound or laser. Colors may be also used in color code to link or "intertwine" ultrasound/topical treatments and light or laser light treatments into a predetermined sequence and at the appropriate time interval.

In a preferred embodiment of the invention, for example, Step One of the kit may include the following items:

A tear and wipe prepackaged skin pad impregnated with a skin cleanser.

A sterile unpreserved unit dose package, vial, twist off plastic, tear packet, etc. type of container which contains a solution that adjusts the pH of the skin to pH 8.5

A vial of dry enzyme powder (which requires pH 8.5 to properly function).

A small vial of an appropriate amount of sterile distilled unpreserved H$_2$O to add to the dry powder.

A small plastic cup and plastic spatula to mix these in.

All of the items in Step One of the kit may be coded with the same identifying number, letter and/or color.

Step Two of the kit may include a set of instructions to use the coupling gel and ultrasound as per the patient Treatment Card parameters.

Step Three may include the active agent itself, in a sterile single use package, with any additional ancillary items needed for that particular agent.

Step 4 may include the post treatment skin protective regimen which may include the following:

A cleansing agent to remove the specific active agent prepackaged.

A buffering solution to restore the skin to pH 5.5 (if necessary for a given process or active agent).

An environmental protection lotion which may be specially formulated to help protect the skin until it has regained its own barrier function.

A possible nonirritating sun block to use on top of the environmental protective cream.

The present invention has numerous potential beneficial uses. For example, the present invention, in a preferred embodiment, may be useful to directly or indirectly produce beneficial effects by biochemical stimulation of tissue or cells (or thermal events without the use of topical agents) including such activities as stimulating fibroblast production of new collagen or elastic fibers. The present invention, in a preferred embodiment, may be useful to lighten uneven or extra pigment (including melanin) in the epidermis or dermis. The present invention may be useful to add, augment or supplement antioxidants, vitamins, phytonutrients, trace elements, minerals, or naturally occurring, synthetic or generically engineered substances which may alter or improve the structure, health or function of the skin or subcutaneous tissue.

The present invention, in a preferred embodiment, may be useful to: deliver agents which enhance, speed or promote wound healing; deliver anesthetic agents to the skin and subcutaneous tissues; improve skin tone and "tighten" loose skin; to reduce the appearance of cellulite; reduce wrinkles or scars; deliver drugs for the purpose of producing a non-local, systemic effect (such as insulin); deliver agents in their pure or neat form of in vehicles such as gels, creams, ointments, emulsions, micropolymer beads (or sponges, etc.), liposomes or other natural or synthetic "transport device" used with or without a coupling media.

The present invention provides the possibility for the non-surgical rejuvenation of skin, improved wound healing, better anesthetic for cutaneous surgery without needles, delivery of drugs that currently are ineffective or poorly tolerated by topical delivery. In other words, the present invention may be useful for improving the absorption of drugs or other substance which were previously inefficiently absorbed, and for allowing the absorption of drugs or other substances which were previously not absorbable at all.

As used herein, the term "light therapy in accordance with the present invention" includes, but is not limited to, laser light therapy and low energy laser light therapy (also occasionally referred to as "low light therapy" or "LLT"). In general, laser light may be characterized as "coherent" light, whereas non-laser light may be characterized as "non-coherent" light. The present invention encompasses therapeutic uses of both "coherent" and "non-coherent" light.

As used herein, the term "cell" or "cells" includes, but is not limited to, cells of virtually any living organism, including human cells, mammalian animal cells, non-mammalian animal cells and plant cells.

The present invention, in a preferred embodiment, may be useful to biostimulate cells or fibroblasts (including fetal fibroblasts). Although the precise mechanism by which such biostimulation occurs is not fully understood, it appears that some part of the energy producing portion of the cells may be stimulated by light. Using different wavelengths, different energy parameters, etc., for different cell types. The present invention, in a preferred embodiment, may be useful to stimulate, or inhibit, many different living cells (not just human cells and not just human fibroblasts). Possible "targets" within the cell itself might include, for example: mitochondria, cytochrome system, ferrodoxin absorption (redox reactions). Biostimulation of fibroblasts (including fetal fibroblasts) may affect production of ATP for cell energy, may work on other cells with mitochondria, and may be able to inhibit certain cell functions (e.g. decrease production of scar tissue, slow growth of cancer or tumor cells, etc) as well as stimulate.

Light therapy in accordance with the present invention probably produces biostimulation in an energy range of from about 0.01 to about 5.0 Joules/cm$^2$ and perhaps up to about 10 Joules/cm$^2$. Inhibition probably extends from about 5.0 to about 10.0 Joules/cm$^2$ or perhaps higher in some cases.

The present invention, in a preferred embodiment, may be useful to specifically stimulate (or inhibit) the growth of hair or other skin appendages (such as nails, etc). The present invention, in a preferred embodiment, may also be useful to stimulate the growth, or re-growth, of fine vellus or dormant or inactive hairs (e.g. to treat hair loss, for example). For example, the present invention may be useful to enhance the effectiveness of Rogaine or similar drugs used in the treatment of male pattern baldness.

The present invention, in a preferred embodiment, may be useful to stimulate (or inhibit) the growth of other cells. Various laser parameters may be matched to those effective for the particular cells being treated. These laser parameters may include wavelength, energy fluence, pulse duration, time of exposure, frequency of exposure, etc.

The present invention, in a preferred embodiment, may be useful to stimulate cell activity, such as stimulating fibroblasts (including fetal fibroblasts) to produce collagen and elastin, for example. The present invention, in a preferred embodiment, may be useful to stimulate cell proliferation or multiplication, such as stimulating native, transplanted, foreign or bioengineered fibroblasts, for example. The present invention may further be useful to stimulate simultaneously both cell activity and cell proliferation.

The present invention, in a preferred embodiment, may be useful to affect abnormal cells, such as benign or malignant cells, by inhibiting (or stimulating) tumor growth. The stimulation may be achieved either directly or indirectly, through interaction with an added substance. Such added substances might include, for example, chemicals, dyes, hormones, genetically engineered substances, plant derived materials, synthetic human materials (such as synthetic melanin), etc. The added substances may be effective inside or outside the cell, and may be incorporated into cells or structures by various methods. The present invention, in a preferred embodiment, may also be useful to affect organ regeneration.

The present invention, in a preferred embodiment, may be useful to affect or modify cells which have been manipulated or altered (by genetic engineering or other cell modification technology) so that the cells may be stimulated or inhibited. Cells may be made more or less productive, active, to multiply, to die, etc., so that the cells respond more favorably than normal or native cells to any of the processes described herein. This could make subcellular components, systems, or organelles behave in like manner as described above (e.g. could make the cell "energy factories"—the mitochondria— more productive or photoactive, etc., or make changes to cellular DNA and/or RNA that would alter response to treatments described herein). Changes in the telomere may alter the cellular division "limit" or remove limits on the functioning or multiplication capabilities of selected cells or cell lines.

The present invention, in a preferred embodiment, may be useful to insert, inject, or otherwise place fibroblasts (including fetal, autologous, donor, or genetically engineered fibroblasts) into the skin (or into wounds, etc), associated with a collagen (including fetal collagen), synthetic or bioengineered matrix. Light therapy, ultrasound therapy, topicals, or a combination of these may be useful to stimulate the treated area. Current commercially available materials that may be used for this purpose may include, for example, Appligraf, Dermologen, Isolagen, Zyderm, Zyplast, and other similar products or mixtures thereof. For example, the present invention may be useful to treat chronic skin ulcers. Such skin ulcers may be pretreated in accordance with the present invention to prepare or stimulate the wound bed. Appligraf may then be applied. The ulcers may be postreated in accordance with the present invention to stimulate or activate fibroblasts (including fetal fibroblasts) and to enhance wound healing. Meanwhile, the treatment may be supplemented by providing precursor substance intravenously.

The present invention, in a preferred embodiment, may be useful to add "precursor substances" in appropriate concentrations, forms, etc. that may enhance or facilitate appropriate metabolic pathways. The precursor substances may be added prior to, during, after, or at any time relative to the time of treatment(s) to maximize the effects of stimulation (or inhibition) by light therapy or ultrasound therapy (or both, since ultrasound therapy may help enhance permeability for large molecules). The maximum effectiveness of a product may thereby be obtained from the stimulation (inhibition). Such precursor substances may include, but are not limited to, chemicals, enzymes, cofactors, etc. (For example, for collagen (including fetal collagen) synthesis the precursor substances may include: ascorbic acid, iron, proline, hydroxyproline, etc.). Such precursor substances could also be oral or parenteral (e.g., delivered intravenously for wound healing).

It is also possible to add (any route, not just skin) inhibitors of breakdown of the substance whose increased production is desired (e.g. For elastin could use substances which inhibit elastase enzyme. For collagen (including fetal collagen) could use inhibitors of metalloproteinases also formerly known as collagenases). These inhibitors could be direct or could work in an indirect manner to either increase activity/quantity of other native or exogenously added inhibitors or to decrease activity/quantity of the substance that produces the breakdown.

The present invention, in a preferred embodiment, may be useful to stimulate or activate new skin substitutes, wound healing agents or dressings that contain fibroblasts (e.g. Appligraf).

The present invention, in a preferred embodiment, may be useful to directly stimulate (or inhibit) the hair follicle itself or to deliver stimulating substances to the follicle or perifollicular support structures, including follicle vascular supply. For example, the present invention may be useful to enhance the healing of transplanted hair and/or to stimulate the growth of transplanted hairs. Similarly, the present invention may be useful to enhance the survival of and/or improve the healing of skin grafts and tissue transfers.

The present invention, in a preferred embodiment, may be useful to stimulate or inhibit (through the eye or through the skin, perhaps via blood vessels close to skin surface) endogenous hormone activities (e.g. melatonin production) or drugs in order to affect, alter, adjust sleep cycles, jet lag, insomnia, and perhaps seasonal affective disorder or even depression. For example, a small electronic unit in accordance with the present invention and containing a fiber optic device or LED could be strapped to a traveler's arm or leg before, during and/or after jet travel to help reduce or eliminate the effects of jet lag.

The present invention, in a preferred embodiment, may be useful to affect certain infectious processes where the organisms may be reachable by these techniques and also where the organisms may be susceptible to being reduced or killed by light stimulation or simply by heat itself from either of these modalities (e.g., nail fungal infections, chronic wounds, venous or diabetic ulcers, etc.).

The present invention, in a preferred embodiment, may also be delivered by using, whether serially or simultaneously, different wavelengths of light or multiple wavelengths of light (with either same or different parameters).

The present invention, in a preferred embodiment, may be useful in targeting amino acids in the hair shaft. For example, the present invention could be used to facilitate the destruction of hairs (hair removal) or to stimulate hair activity (growth or regrowth of hair) or to affect the cosmetic appearance or style of hair. The present invention may be useful in altering the amino acids in hair to change the color and/or the curliness or straightness of the hair.

The present invention, in a preferred embodiment, may be useful in delaying aging, or at least delaying the outward appearance or cosmetic manifestations of aging in skin and other cells and tissues. Preventing or diminishing the production or activity of skin matrix metalloproteinases (MMP) may help to prevent or diminish the degradation of existing or newly formed collagen and skin dermal matrix. The present invention may be useful as periodic treatment to counter the adverse effects of photaging.

Various processes and events produce or promote their activities. For example, ultraviolet light exposure produces photoaging of the skin and solar scarring of the skin.

If the objective is to stimulate the production of new collagen, or to inject or implant fibroblasts (or cover a wound with them) with or without being kept on a latticework or matrix of some type of already formed collagen, then premature degradation is undesirable. Likewise, degradation of the newly formed collagen is undesirable.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for enhancing the transport of an active agent through mammalian skin, wherein the skin comprises a stratum corneum, the method comprising:

exposing the skin to ultrasound, applying an active agent to the skin, and modifying at least portion of the stratum corneum substantially prior to the step of exposing the skin to ultrasound, wherein the step of modifying at least a portion of the stratum corneum comprises at least one of the steps of:

removing at least a follicular plug from the stratum corneum, removing at least skin debris from the stratum corneum, and removing at least a portion of the stratum corneum, wherein the stratum corneum is characterized by a structure, a function, a thickness and a permeability and wherein the step of modifying at least a portion of the stratum corneum comprises at least one of the steps of stripping, removing, thinning and diminishing at least one of the structure, function, thickness and permeability of the stratum corneum by at least one of a mechanical, abrasive, photo acoustic, ablative, thermal, chemical, abrasive and enzymatic method.

* * * * *